United States Patent [19]

Bombardelli

[11] 4,157,894
[45] Jun. 12, 1979

[54] PRODUCTION AND ANALYSIS OF GINSENG ROOT EXTRACT

[75] Inventor: Ezio Bombardelli, Milan, Italy

[73] Assignee: Inverni della Beffa S.p.A., Milan, Italy

[21] Appl. No.: 801,398

[22] Filed: May 27, 1977

[30] Foreign Application Priority Data

Jun. 3, 1976 [GB] United Kingdom ............... 23021/76

[51] Int. Cl.$^2$ ......................... G01N 31/08; C07J 17/00
[52] U.S. Cl. ................................. 23/230 R; 424/182; 536/5
[58] Field of Search ...................... 23/230 R; 536/5; 424/182

[56] References Cited

U.S. PATENT DOCUMENTS

| | | | |
|---|---|---|---|
| 3,464,972 | 9/1969 | Rocher | 424/182 X |
| 3,883,425 | 5/1975 | Dorn | 536/5 X |
| 3,886,272 | 5/1975 | Parkhurst | 536/5 X |
| 3,901,875 | 8/1975 | Park | 536/5 |

OTHER PUBLICATIONS

Kondo et al., Chem. Absts. 9-2793$^4$, (1915).
Baladin et al., Chem. Absts. 53-8319i, (1959).
Eisler, M., Chem. Absts. 20-3744$^4$, (1926).
Seide et al., Gas Chromat. Absts., 1970, No. 845.
Kondo et al., Chem. Absts. 69-77689p, (1968).
Dalsgaard, K., Chem. Absts. 74-67744s, (1971).
Lutomski et al., Chem. Absts. 85-174295v, (1976).
Bell et al., Chem. Absts. 80-112563u, (1974).
Bombardelli et al., Chem. Abstrs. 86-13818y, (1977).
Sakamato et al., Chem. Absts. 84-95665s, (1976).

*Primary Examiner*—Sidney Marantz
*Attorney, Agent, or Firm*—Browdy and Neimark

[57] ABSTRACT

A method for producing a purified extract of ginseng root which comprises contacting an aqueous extract of ginseng root with a solid absorption resin so as to absorb active saponins contained in the extract on the resin and eluting active saponins from the resin.

Also a method of analyzing a ginseng extract which comprises subjecting the extract to silylation to convert saponins contained in the extract to trimethylsilyl ethers, separating the ethers by gas-liquid chromatography and detecting the separated ethers.

7 Claims, 1 Drawing Figure

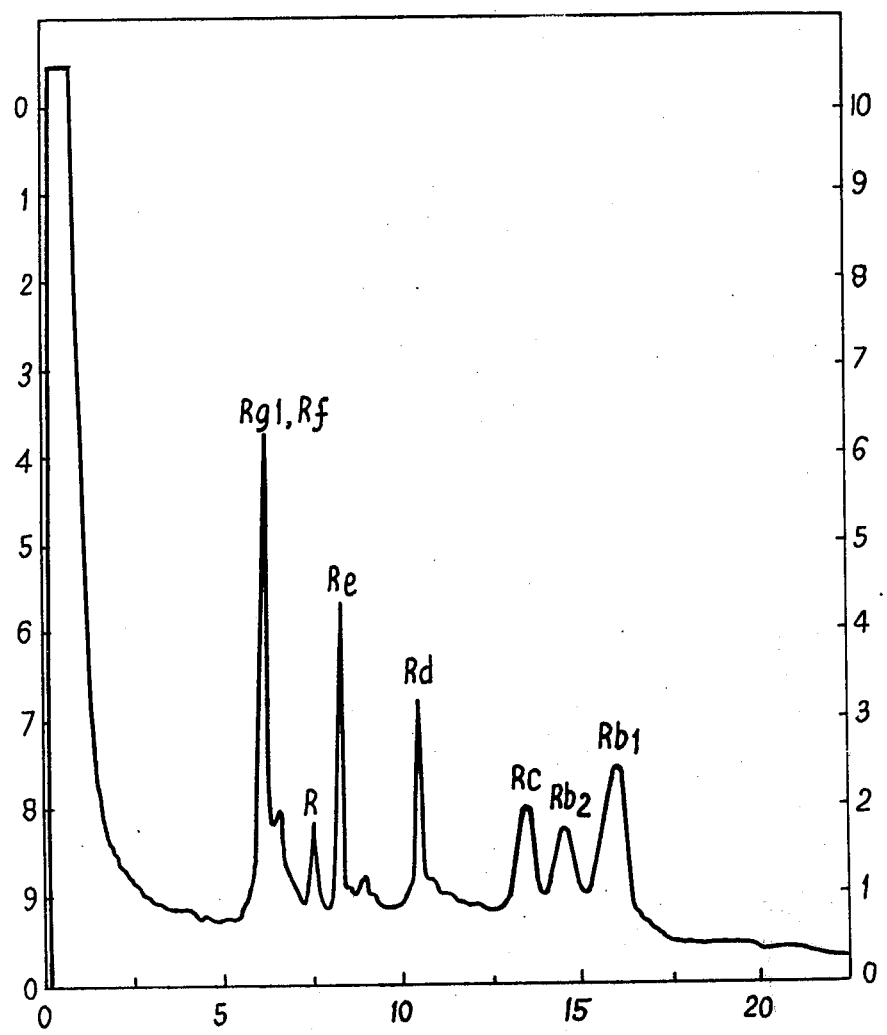

PRODUCTION AND ANALYSIS OF GINSENG ROOT EXTRACT

FIELD OF THE INVENTION

This invention relates to methods for producing purified and standardized ginseng extracts. More specifically, the invention relates to a method for purifying extracts of ginseng, to the purified extracts so obtained and to an analytical method for standardizing ginseng extracts.

BACKGROUND OF THE INVENTION

The roots of ginseng (*Panax ginseng*, C. A. Mayer and other species) are widely used in the pharmaceutical, dietetic and cosmetic fields, either as such (for example pulverised for the preparation of infusions and decoctions) or in the form of derivatives such as, for example, extracts of various types (e.g. alcoholic or aqueous extracts either in liquid form or dried or atomized).

In view primarily of the variable nature of the roots, the lack of selectivity of the available extraction methods, and also the absence of a convenient method of analysis, presently available extracts do not have a sufficient constancy of activity, and thus of treatment effect.

SUMMARY OF THE INVENTION

We have now developed a purification method which enables ginseng extracts to be produced in a straightforward manner which are enriched in the active principles of the starting material to an extent which has not been achieved hitherto and also an analytical procedure which enables these active principles, and even individual components thereof, to be monitored.

BRIEF DESCRIPTION OF DRAWING

The sole FIGURE is a chromatogram showing the analysis by gas chromatography of a product produced in accordance with the present invention.

DESCRIPTION OF THE PREFERRED EMBODIMENTS

Thus according to one aspect of the present invention, there is provided a method for obtaining a purified extract of ginseng root which comprises contacting an aqueous extract of ginseng root with a solid absorption resin so as to absorb active saponins contained in the extract on the resin, and eluting active saponins from the resin.

Prior to eluting the active saponins, the solid absorption resin with the active saponins absorbed thereon may be separated from the remainder of the extract in any convenient manner, although preferably the contacting with the resin and the separation is effected by passing the aqueous extract through a column or bed of the resin.

Preferably, the solid absorption resin comprises an aromatic polymer, i.e. a polymeric material containing a plurality of aromatic (e.g. benzene) groups bonded into a polymeric chain. Specific examples of absorption resins which may be used in carrying out the process of the invention are polystyrene absorption resins, for example the cross-linked polystyrene absorption resin "Amberlite XAD-2" sold by Rohm and Haas, and phenol-formaldehyde absorption resins, for example "Duolite S-30" sold by Diamond Alkali Company.

It is desirable that the solid absorption resin used to absorb the active saponins should be essentially free of strongly acidic or basic groups, so as to avoid absorbing ionic impurities contained in the original extract. I.e. the solid absorption resin preferably should not possess strong ion-exchange properties.

As indicated, the contacting of the aqueous extract of ginseng roots with the absorption resin and the separation of the absorption resin (and absorbed active saponins) from the remaining extract is preferably carried out by passing the extract through a column or bed of the absorption resin.

Various eluants may be employed to recover the active saponins from the resin, but preferably a lower alcohol is used, either as such or in admixture with water and/or other organic solvents.

Where the initial contacting with the solid absorption resin is carried out by passing the extract through a column or bed of resin, the elution may also be effected by simply trickling the elution solvent through the column or bed.

Preferably, prior to contacting the extract with the absorption resin, the extract is subjected to one or more preliminary purification treatments, for example treatment with ion exchange resins and other absorbants to effect a preliminary purification by absorption of the impurities on the ion exchange resins or absorbants, the active saponins remaining in solution in the extract.

The process of the invention enables purified extracts of ginseng root to be obtained which are remarkably free from the various inert substances (salts, sugars, phenols, etc.) which are normally present in raw extracts of the roots and also enables extracts to be obtained which are more concentrated as regards the content of active saponin. For example purified extracts may be obtained containing in excess of 50% by weight of active saponins (expressed as 6,20-diglucosyl-panaxatriol).

In order to obtain the purified extracts in dry form, the elution solvent may be eliminated by conventional methods, for example dessication in vacuo, atomization or freeze-drying. The dry extracts so obtained are generally perfectly soluble in water.

The purified extracts produced in accordance with the invention may be formulated into pharmaceutical compositions by mixing with a suitable diluent or carrier and such compositions form a further aspect of the present invention.

The saponin content of the extracts may be monitored by colorimetric methods, for example after reaction with antimony chloride in 60% perchloric acid or by thin-layer chromatography using silica-gel plates and a 65:35:10 (by volume) elution mixture of chloroform, methanol and water.

These analytical methods are comparatively crude and we have developed a method of analysis which is particularly accurate and also enables the relative proportions of the various saponins forming the active principles of ginseng extracts to be determined.

Thus according to a further aspect of the invention, there is provided a method of analyzing a ginseng extract which comprises subjecting the ginseng extract to silylation to convert saponins contained in the extract to trimethylsilyl ethers, separating the ethers by gas-liquid chromatography and detecting the separated ethers.

Known silylation techniques may be employed to convert the saponins to trimethylsilyl ethers, for example reaction with a mixture of trimethylchlorosilane, N,O-bis-(trimethylsilyl)-acetamide and trimethylsilylimidazole.

Various detection methods may be used to detect the separated ethers, for example, a convenient technique is to use a hydrogen flame ionization detector. A mass spectrographic detector may also be used.

The method of analysis of the invention enables the presence in ginseng extracts of the various active saponins to be estimated both qualitatively and quantitatively. In particular the known active saponins referred to as $Rb_1$, $Rb_2$, Rc, Rd, Re, Rf and Rg have been determined. The structures of the components is given in the following Table:

After freeze-drying, 55 g. of purified dry extract of ginseng were obtained having a content of 65% of saponins.

EXAMPLE 3

10 kg. of finely ground roots of Panax ginseng were extracted in accordance with the procedure of Example 1.

The aqueous concentrate was chromatographed on a column containing 1 kg. of strong anionic resin (quaternary ammonium salt) and then on a column containing

TABLE

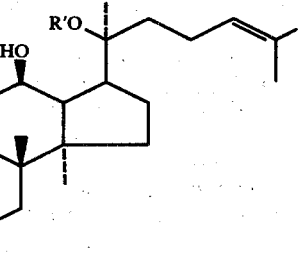
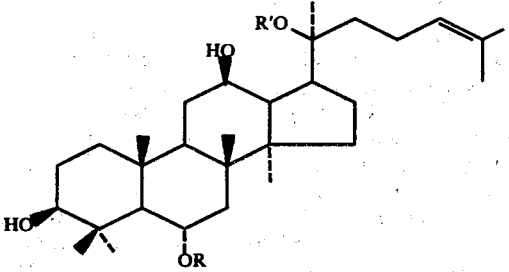

20 S-Protopanaxadiol    R = R' = H
20 S-Protopanaxatriol   R = R' = H

Ginsenoside $Rb_1$
- R = D—Glc—β(1→2)D—Glc—
- R' = D—Glc—β(1→6)D—Glc—

Ginsenoside Re
- R = L—Rha(1→2)D—Glc—
- R' = D—Glc—

$Rb_2$
- R = D—Glc—β(1→2)D—Glc—
- R' = L—Ara(pyranose)β(1→6)—D—Glc—

Rf
- R = D—Glc—β(1→2)—D—Glc—
- R' = D—Glc—

Rc
- R = D—Glc—β(1→2)D—Glc—
- R' = L—Ara(furanose)β(1→6)—D—Glc—

$Rg_1$
- R = D—Glc—
- R' = D—Glc—

Rd
- R = D—Glc—β(1→2)—D—Glc—
- R' = D—Glc—

Saponins of Panax ginseng

The purification of ginseng extracts according to the present invention will be described in more detail in the following examples:

EXAMPLE 1

10 kg. of ground roots of Panax ginseng were extracted three times at 60° C. with agitation, with 50 liters of 20% aqueous alcohol.

The extraction liquids were concentrated to about 30 liters and the solution clarified with "Celite" and passed through a column containing 3 kg. of phenol-formaldehyde absorption resin ("Duolite S-30").

The column was washed with water until there was no dry residue in the washing liquid and then the saponins were eluted with 70% alcohol. The alcohol was eliminated by evaporation and the aqueous concentrate freeze-dried.

250 g. of purified dry extract of ginseng were obtained having a content of 55% of saponins.

EXAMPLE 2

800 g. of dry hydroalcoholic extract of ginseng, containing 6% of saponins, were dissolved in 50 liters of water. The solution was clarified with Celite and passed over 3.5 kg. of polystyrene absorption resin ("Amberlite" XAD2). Elution was effected as indicated in Example 1, using 60% methanol as eluant for the saponins.

5 kg. of the polystyrene absorption resin used in Example 2.

The column was then washed with de-mineralized water until the washing liquid contained no residue.

The column was then eluted with anhydrous methanol.

The methanol solution was concentrated to 1 liter, diluted with 0.5 liters of water and atomised.

200 g. of purified dry extract were obtained containing 75% of saponins.

The purified extracts of ginseng obtained as described above have particularly low toxicity (LD50=600 mg/kg intraperitoneally and >1000 mg/kg orally in the rat). The extracts have marked stimulating activity on the central nervous system and increase the resistance of the organism to fatigue.

The extracts may be formulated into a wide variety of types of pharmaceutical preparation. Thus sweets, sugar-coated tablets, soft gelatine capsules, hard gelatine capsules, syrups, ointments can be prepared. This product can be used alone or in association with other medicaments useful in the field of use, such as vitamins, steroids, psychoactive drugs, etc.

The following examples illustrate suitable form of pharmaceutical preparation.

EXAMPLE 4

Tablets

Each tablet contains:
Purified and standardized dry extract of ginseng containing 60% saponins  25 mg.

Excipients (starch, lactose, silica powder, magnesium stearate)  q.s. to 120 mg.

EXAMPLE 5

Soft gelatine capsules

Each soft gelatine capsule of 190 mg. contains:
Purified and standardized dry extract of ginseng, containing 70% saponins  20 mg.

Excipients (vegetable oils, soya lecithin) q.s.

EXAMPLE 6

Syrup

Each 100 g. of syrup contain:
Purified and standardized dry extract of ginseng containing 60% saponins  0.250 g.

Excipients (sorbitol, alcohol, flavourings, water) q.s.

EXAMPLE 7

Ointment

An ointment, each 100 g. of which contained the following ingredients, was prepared:
Purified and standardized dry extract of ginseng containing 60% saponins  2 g.

Excipients (tween 80, sodium lauryl sulphate, spermaceti, mixture of fatty alcohols and hydrocarbons, hydrogenated lanolin, sodium alginate, stearin, purified water)  q.s 100 g.

EXAMPLE 8

Soluble granules

Purified and standardised dry extract of ginseng containing 60% saponins  40 mg.

Excipients (mannitol, lactose, surcrose, flavourings) g.

EXAMPLE 9

Drops

Purified and standardized dry extract of ginseng containing 60% saponins  200 mg.

Excipients (alcohol, propylene glycol, tween 80, purified water)  q.s to 10 ml.

EXAMPLE 10

Lyophilized ampoules

Purified and standardised dry extract of ginseng containing 60% saponins  10 mg

Excipient (mannitol)  50 mg

Solvent
Water for injection  2 ml

The following examples illustrate the analytical method of the invention:

EXAMPLE 11

20 mg. of the product of Example 1 were heated with 0.1 ml. of TBT (trimethylchlorosilane, N,O-bis-(trimethylsilyl) acetamide, trimethylsilylimidazole 2:3:3 mixture) for 10 minutes in a screw-capped vial with PTFE liners at 50° C. in 0.1 ml. of pyridine.

1 mg. of the resulting solution was analyzed by gas chromatography on a Varian 1400 aerograph gas chromatograph equipped with a hydrogen flame ionization detector.

The following conditions were used:

| | |
|---|---|
| Column length | 0.25 m. |
| Stationary phase | 0.5% OV - 101 (silicon oil - Supelco Inc.) - Chromosorb support WHP. 100–120 mesh (Supelco Inc.) |
| Conveyor gas | Helium |
| Column temperature | Programmed from 240° to 320° C. (8°/min.) |

The resulting chromatogram is shown in the accompanying drawing, from which it can be seen that the various active saponins are well resolved, thus enabling the saponin content of an extract to be determined with high accuracy. By using this technique, the saponin content of ginseng extracts can be readily monitored and adjusted as required to give a standard product.

The purified products of the invention, particularly when standardized as described above are particularly advantageous in enabling pharmaceutical forms of low volume and high, constant activity to be prepared.

This feature is especially useful in the geriatric field, where presently available extracts, due to their low content of active saponins, require the administration of high unitary doses and thus the preparation of pharmaceutical forms (capsules, sweets, sugarcoated tablets etc.) of large volume which are poorly accepted by elderly patients who frequently have difficulty with digestion.

I claim:

1. A method for producing a purified extract of ginseng root which comprises contacting an aqueous extract of ginseng root with a solid absorption resin comprising an aromatic polymer selected from the group consisting of polystyrene and phenol-formaldehyde resins so as to absorb active saponins contained in the extract on the resin and eluting active saponins from the resin.

2. A method according to claim 1 in which the aqueous extract is contacted with the solid absorption resin by passing the extract through a column or bed of the resin.

3. A method according to claim 1 in which the active saponins are eluted using a solvent comprising a lower alcohol as eluent.

4. A method according to claim 1 in which prior to contacting the extract with the absorption resin the extract is subjected to a preliminary purification treatment comprising contacting the extract with an ion exchange resin.

5. A method of analysing a ginseng extract which comprises subjecting the extract to silylation to convert non-hydrolysed saponins selected from the group consisting of ginsenosides $Rb_1$, $Rb_2$, Rc, Rd, Re, Rf and $Rg_1$ contained in the extract to trimethylsilyl ethers, separating the ethers by gas-liquid chromotography and detecting the separated ethers.

6. A method according to claim 5 in which the saponins are converted to trimethylsilyl ethers by reaction with a mixture of trimethylchlorosilane, N,O-bis-(trimethylsilyl)-acetamide and trimethylsilylimidazole.

7. A method according to claim 5 in which the separated ethers are detected using a hydrogen flame ionization detector or a mass spectrographic detector.